US008557304B2

(12) United States Patent
Hoerl et al.

(10) Patent No.: US 8,557,304 B2
(45) Date of Patent: Oct. 15, 2013

(54) METHOD OF OBTAINING SECONDARY PLANT CONSTITUENTS

(75) Inventors: Hans-Heinrich Hoerl, Bovenden (DE); Wolfgang Demmer, Goettingen (DE); Rene Faber, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 13/319,552

(22) PCT Filed: Apr. 23, 2010

(86) PCT No.: PCT/EP2010/002497
§ 371 (c)(1),
(2), (4) Date: Nov. 9, 2011

(87) PCT Pub. No.: WO2010/142364
PCT Pub. Date: Dec. 16, 2010

(65) Prior Publication Data
US 2012/0077994 A1  Mar. 29, 2012

(30) Foreign Application Priority Data
Jun. 9, 2009  (DE) .................. 10 2009 024 410

(51) Int. Cl.
*A61K 36/00* (2006.01)
(52) U.S. Cl.
USPC ........... 424/725; 424/777; 424/776; 424/778; 424/773; 424/774; 424/779
(58) Field of Classification Search
None
See application file for complete search history.

(56) References Cited

U.S. PATENT DOCUMENTS

| 5,141,611 A | 8/1992 | Ford |
| 5,886,155 A | 3/1999 | Armah et al. |
| 2005/0208637 A1* | 9/2005 | Demmer et al. .............. 435/183 |

FOREIGN PATENT DOCUMENTS

| DE | 24 44 947 | 3/1975 |
| EP | 0 806 474 | 11/1997 |
| GB | 1 483 088 | 8/1977 |
| WO | 00/45769 | 8/2000 |
| WO | 2008/097154 | 8/2008 |
| WO | 2008/136741 | 11/2008 |

OTHER PUBLICATIONS

Bongartz et al, Selective extraction of quercetrin in vegetable drugs and urine by off-line coupling of boronic acid affinity chromatography and high-performance liquid chromatography. Journal of Chromatography, B: Biomedical Applications (1995), 673(2), 223-30.*
Affi-Gel 601 description from Bio-Rad, accessed on Feb. 6, 2013, pp. 1-2.*
Zhao et al, Separation and quantification of flavonoid compounds in Rhododendron anthopogonoides Maxim by high-performance liquid chromatography. Acta Chromatographica (2008) vol. 20, No. 1, pp. 135-146.*
Journal of Membrane Science 134 (1997), 191-197, Z. Borneman et al.
International Preliminary Report.

* cited by examiner

Primary Examiner — Qiuwen Mi
(74) Attorney, Agent, or Firm — Gerald E. Hespos; Michael J. Porco; Matthew T. Hespos

(57) ABSTRACT

The present invention relates to a method of isolating phenolic secondary plant constituents from plant material using a microporous membrane which displays affinity ligands for the phenolic secondary plant constituents.

14 Claims, No Drawings

METHOD OF OBTAINING SECONDARY PLANT CONSTITUENTS

BACKGROUND OF THE INVENTION

1. Field of the Invention

The present invention relates to a method of isolating phenolic secondary plant constituents from plant material, and to a food additive obtainable by this method.

2. Description of the Related Art

Plant constituents, in particular what are known as the secondary plant constituents, which have no substantial calorific value, have increasingly attracted the attention of science and food technology, where they are of interest as food supplements or food additives by the key phrase "functional food".

The compounds which are of particular importance in this context are low-molecular-weight compounds which have antioxidative properties and, as a consequence, are capable of inactivating the ubiquitously generated so-called "reactive oxygen species", that is reactive oxygen-comprising molecules such as, for example, hydroxyl radicals OH., the superoxide anion $O_2^-$, hydrogen peroxide $H_2O_2$, singlet oxygen which is capable of reacting with nitrogen monoxide NO to give peroxynitrite $ONO_2$, and hypobromite and hypochlorite. Further positive effects of these low-molecular-weight compounds which are discussed intensively in connection with their antioxidative activity are, for example, the protection of endothelial cells, the suppression of tumor growth and the protection of the cardiovascular system. The cardioprotective activity, for example, which is associated with the regular consumption of red wine, is caused, inter alia, by diphenols which are substituted by OH groups, such as, for example, resveratrol. Resveratrol is a substance which, in turn, probably acts as an antioxidant and lowers the oxidation sensitivity of low-density lipoprotein (LDL) in the blood, inhibits platelet aggregation and inhibits the endogenous cholesterol biosynthesis by inhibiting the squalene monooxygenase enzyme.

The technical isolation, or obtaining, secondary plant constituents makes particularly high demands on the work-up thereof since the stability of many isolated substances declines rapidly above a certain pH. Since in addition many plant extracts have a high fruit acid and ion content, separation via traditional ion-exchange chromatography is made difficult or indeed impossible. Furthermore, methods known from the prior art frequently require large volumes of plant extract to be employed, require toxicologically unacceptable, or caustic, substances such as methanol or acetic acid for eluting the secondary plant constituents, and are frequently very time-consuming. In contrast, the limited storage stability of many secondary plant constituents requires rapid process steps so as to be able to transfer the sensitive substances as quickly as possible into a stabilizing medium.

An example which is known from the prior art is a method of concentrating anthocyanin from blueberry juice concentrate by means of a strongly hydrophobic Amberlite® XAD column with a length of two meters and a diameter of 11 cm. The disadvantages of this method, however, are the required high volumes of juice concentrate to be employed, the elution with toxicologically unacceptable, or caustic, substances such as methanol and acetic acid, and the high expenditure of time for separating the anthocyanins from the juice concentrate.

WO 2008/136741 A1 discloses a method for removing polyphenols from beverages, in which the beverages are treated with a polymer matrix to which ether ligands, preferably polyether ligands with multiple CC bonds, are fixed. The polymer matrix may be present as a particulate or membrane-shaped adsorbent.

WO 2008/097154 A1 discloses a method for removing turbidity-causing materials from beverages. The polymer matrices which are used are based on crosslinked polysaccharides and are provided with a polyether coating which can be generated by grafting for example polyethylene glycol or diethylene glycol vinyl ether. Providing the matrices with polyether functions makes possible the efficient removal of undesired polyphenols from beverages, where the polyphenols do not constitute target products of the method.

U.S. Pat. No. 5,141,611 discloses a method of removing polyphenols from beverages, where polyamide membranes or polyamide particles with a surface modification based on glutaraldehyde/resorcinol or based on glutaraldehyde in combination with melamine, 1,6-hexamethylenediamine or various amino acids, are used.

EP 0 806 474 A1 discloses a method in which Sepharose-based chromatography gels which have cation-exchanging ligands (sulfopropyl or carboxymethyl groups) are used for removing turbidity from beverages or for stabilizing beverages. In this method, polyphenols together with companion proteins, being undesired contaminants, are removed from beer. It is furthermore disclosed how the cation exchangers can be regenerated for reuse by the action of water, sodium hydroxide solution or saline. The method disclosed in EP 0 806 474 A1 does not contain any steps which permit the isolation of the polyphenols as target substances, i.e. steps which permit the removal of the polyphenols from the accompanying proteins or other contaminants from beer production.

U.S. Pat. No. 5,886,155 discloses a method for the adsorptive removal of tannins and polyphenols from protein mixtures of vegetable origin by means of hydrophobic interaction chromatography (HIC), with the target proteins being eluted from the HIC matrix, and the subsequent purification of the target proteins by means of a second step of hydrophobic interaction chromatography.

WO 00/45769 A2 discloses a method for isolating polyphenolic antioxidants from a purin-comprising plant extract, where the antioxidants are selectively adsorbed to a matrix which is composed of polyvinylpolypyrrolidone, chitosan or mixtures of these, and where the matrix is present for example as a chromatography resin.

In Journal of Membrane Science 134 (1997), 191-197, Z. Borneman et al. disclose a method for removing polyphenols, and of a brown coloration associated with the presence of these polyphenols, from apple juice. As regards the removal of these polyphenols, polyether sulfone membranes (PES) which are modified with polyvinylpyrrolidone outperform membranes of regenerated cellulose which has no ligands fixed to it. Fouling phenomena which are observed on the PES membrane during the method can be reversed by regenerating the membrane with sodium hydroxide solution.

SUMMARY OF THE INVENTION

The present invention is therefore based on the object of providing a method of isolating secondary plant constituents from plant material, which method can be carried out in a simple manner, with a low expenditure of time and at low pH values. It is also intended that this method avoids the use of toxicologically unacceptable solvents and the use of large solvent volumes for isolating the secondary plant constituents.

This problem is solved by the embodiments of the present invention which are characterized in the claims. In particular, there is provided in accordance with the invention a method of isolating secondary plant constituents from plant material, which method meets the above requirements. In this context it has been found, surprisingly, that the use of microporous membranes which carry group-specific affinity ligands makes possible the extraction of secondary plant constituents from plant material.

DETAILED DESCRIPTION OF THE PREFERRED EMBODIMENTS

A subject matter of the present invention relates to a method of isolating phenolic secondary plant constituents from plant material, comprising the steps of:

(a) providing a plant extract from plant material which comprises phenolic secondary plant constituents, (b) bringing the plant extract into contact with a microporous membrane which has affinity ligands for the phenolic secondary plant constituents, whereby the phenolic secondary plant constituents are adsorbed on the membrane, and (c) eluting the phenolic secondary plant constituents from the membrane, whereby a solution comprising the phenolic secondary plant constituents is obtained.

In accordance with the invention, the expression "to isolate" also comprises obtaining a solution which comprises the phenolic secondary plant constituents. The phenolic secondary plant constituents can, if appropriate, be purified further from this solution, and/or the phenolic secondary plant constituents can be obtained as such by removing the solvent.

In accordance with the invention, the expression "plant material" comprises any plant material which comprises phenolic secondary plant constituents. In a preferred embodiment, the plant material is selected from the group consisting of fruits, in particular berries, vegetables, legumes, tubers, bulbs, beet/taproots, tea, cacao, coffee, timber, flowers, seeds, leaves and cones of conifers. In an especially preferred embodiment, the plant material is fruit skin.

In accordance with the invention, the expression "secondary plant constituents" comprises chemical compounds which are produced by plants neither in the energy metabolism nor in the anabolism or catabolism, and which preferably serve for the defense against pathogens and herbivores, the protection against environmental factors such as, for example UV radiation, or to attract pollinators and seed dispersers.

In accordance with the present invention, the secondary plant constituents are phenolic compounds. For the purposes of the present invention, phenolic compounds are understood as meaning phenols and phenol derivatives. Such compounds may comprise one or more aromatic rings, it being possible for the aromatic rings to be fused or to be bridged with each other via substituted alkyl groups, it being possible for the derivatives to display further OH groups in addition to the phenolic OH groups. Furthermore, the phenolic OH groups may be derivatized. For example, the phenolic OH groups and/or the further OH groups may be glycosylated. Moreover, the secondary plant constituents may be modified as the result of methylation, acetylation or conversion into their aldehyde or acid function.

The present invention relates to the isolation of any suitable phenolic secondary plant constituents. The secondary plant constituents are preferably selected from the group consisting of phenols; benzoquinones; hydroxybenzoic acids; acetophenones; tyrosine derivatives; phenylacetic acids; hydroxycinnamic acids; coumarins; isocoumarins; chromones; naphthoquinones; xanthones; stilbenes; anthraquinones; flavonoids, in particular flavones, flavonols, flavanols, flavanones, flavanonols, anthocyanins, proanthocyanins, isoflavonoids and biflavonoids; lignans, neolignans; lignins; catechol melanins; betalains; and chalcones.

An example of a preferred phenol is L-DOPA. Examples of preferred hydroxyaryl acids are hydroxybenzoic acids, in particular salicylic acid, 4-hydroxybenzoic acid, gentisic acid, protocatechuic acid, gallic acid, vanillic acid, ellagic acid, hexahydroxydiphenic acid and their esters, in particular tannins, and their dilactones. Examples of preferred hydroxycinnamic acids are coumaric acid, ferulic acid, caffeic acid, sinapic acid, rosmaric acid and their esters and amides. Examples of preferred coumarins are scopoletin, herniarin, aesculetin, fraxetin, coumarin and umbelliferone. An example of a preferred stilbene is resveratrol. Examples of preferred flavonoids are flavones, flavonols, flavanols, flavanones, flavanonols, proanthocyanins and anthocyanins. Examples of preferred flavones in this context are apigenin, luteolin, diosmetin, chrysoeriol, nobiletin, apirgenin, acacetin, galangin, chrysin, tectochrysin, scutellarein, eupatorin, genkwanin, senensetin and their glycosides such as hyperoside, quercitrin and hesperidin. Examples of preferred flavonols are kaempferol, quercetin, myricetin and their arabinosides, galactosides, glucosides, glycosides, rhamnosides and xylosides. Examples of preferred flavanols are catechin, epicatechin, gallocatechin, epigallocatechin, theaflavin and their gallates. Examples of preferred flavanones are isokuranetin, naringenin, hesperitin, eriodictyol and their glycosides, rutinosyl derivatives and neohesperidosyl derivatives. An example of a preferred flavanonol is taxifolin. Examples of preferred proanthocyanins are the glycosides of the procyanidins and prodelphinidins, in particular their gallates. Examples of preferred anthocyanins are the glycosides of pelargonidin, cyanidin, paeonidin, delphinidin, petunidin and malvidin. Examples of preferred isoflavonoids are the isoflavones, in particular the soya isoflavones. Examples of preferred soya isoflavones in this context are genistein, daidzein, glycetein and their glycosides. Examples of preferred lignans are the flax lignans, in particular matairesinol and secoisolariciresinol diglucosides.

Suitable phenolic secondary plant constituents are described, for example, in K. Shetty, G. Paliyath, A. L. Pometto, R. E. Levin, "Functional Foods and Biotechnology", CRC Press LLC 2005, Taylor & Francis Group, pp. 152-159.

Preferred in accordance with the invention among the abovementioned compounds are, in particular, the anthocyanins, i.e. the pigments of various plant parts such as fruit skins, berries or vacuole components, in particular the glycosides of pelargonidin, cyanidin, paeonidin, delphinidin, petunidin and malvidin. Also especially preferred are the proanthocyanins with catechin or epicatechin as their structural base, also in the form of their gallates. A person skilled in the art is familiar with the multiplicity of plant sources for anthocyanins and other secondary plant constituents. A compilation can be found for example in H.-D. Belitz and W. Grosch, "Lehrbuch der Lebensmittelchemie" [Textbook of Food Chemistry], 4th edition, H.-Springer-Verlag Berlin, Heidelberg, New York, 1992, pp. 738-754, ISBN 3-540-55449-1.

Suitable methods for the preparation of plant extracts from plant material are known to the skilled worker; they comprise, for example, the homogenization of plant parts in a disperser or homogenizer.

Before being brought into contact with the membrane, the plant extract may be pretreated, for example by a prefiltration step. Such a prefiltration step serves to remove particles and turbidity-causing substances from the plant extract. In a preferred embodiment of the present invention, however, the plant extract is not subjected to any further pretreatment after its preparation. In particular, the plant extract can be brought into contact with the membrane without prefiltration. In this case, the plant extract comprises particles and turbidity-causing substances, and, owing to these components, may be turbid. The size of the particle is not limiting. In a preferred embodiment of the present invention, the particles present in the plant extract have a size of no more than 0.5 mm. To achieve this, the method according to the invention can, in a preferred embodiment, furthermore comprise, after step (a) and before step (b), the step of:

(a2) homogenizing the plant extract in such a way that the particles present in the plant extract have a size of no more than 0.5 mm.

Suitable homogenization methods are known to the skilled worker. Likewise, the skilled worker knows methods for checking the particle size, for example by checking under the microscope and computer-aided image analysis.

For the purposes of the present invention, the expression "microporous membrane" refers to membranes with a pore size of from 0.1 to 20 μm, preferably from 0.5 to 15 μm and more preferably from 1 to 10 μm. The pore size can be determined using what is known as a "capillary flow porometry test" (Capillary Flow Porometer 6.0, CAPWIN Software System, Porous Materials Inc.).

The microporous membrane can be present in any form which is suitable for the membrane surfaces to come into contact with the plant extract. For example, the microporous membrane can be integrated into a membrane adsorber module. Suitable membrane adsorber modules are known for example from German patent application DE 102 36 664 A1. Preferably, such a membrane adsorber module allows particle to pass, i.e. is resistant to clogging by media comprising particles and turbidity-causing substances.

The integration of the microporous membrane into a membrane adsorber module which allows particles to pass is a particular advantage when a particle-comprising plant extract is used. The particles present in the plant extract will generally not adversely affect the adsorption, on the membrane, of the phenolic secondary plant constituents to be isolated. In this case, a prefiltration step is not necessary, which simplifies the method according to the invention.

All membranes which are capable of adsorbing the phenolic secondary plant constituents may be used as microporous membrane. To this end, the microporous membranes display suitable affinity ligands.

Affinity ligands for phenolic secondary plant constituents which can be used in the method according to the invention are all suitable ligands which are capable of binding OH groups. Suitable OH-group-binding affinity ligands are known to the skilled worker. In a preferred embodiment of the present invention, the affinity ligands are boronates or metal chelates. Especially preferred among the metal chelates are metal complexes of iminodiacetic acid, of N-methyliminodiacetic acid, of N-(hydroxymethyl)iminodiacetic acid, of N-(hydroxyethyl)ethylenediaminetetraacetic acid and combinations of these, in each case preferably as complexes with iron(II) cations (Protein Purification, Second Edition, Principles, High Resolution Methods and Applications, J.-C. Janson, L. Ryden eds., Wiley-VCH 1998, ISBN 0-471-18626-0). Especially preferred affinity ligands are aminophenyl boronate or iron(II) iminodiacetic acid complexes. Methods which are suitable for the derivatization of microporous membranes with affinity ligands are well known to the skilled worker and described, for example, in G. T. Hermanson, A. K. Mallia, P. K. Smith (editors), "Immobilized Affinity Ligand Techniques", Academic Press, San Diego, ISBN 0-12-342330-9.

In a preferred embodiment of the present invention, sodium aminophenylboronate for example is bound via the amino group as the imine/Schiff base to the aldehyde groups of the starting membrane. The two free OH groups of the aminophenylboronate which is fixed to the membrane as a ligand, which are present after the work-up of the finished membrane, permit the subsequent interaction with cis-diols, for example the sugar component of the anthocyanins or proanthocyanins.

A microporous membrane which is suitable for use in the method according to the invention is, for example, a membrane of a cellulose hydrate matrix and pores which extend from one main surface to the other main surface of the membrane, the membrane displaying on its internal and external surfaces functional groups (affinity ligands) for the separation of substances by adsorption.

The starting material used for such a microporous membrane is a cellulose ester membrane which is brought into contact with at least one solution under conditions which, firstly, lead to swelling of the cellulose ester matrix and, secondly, simultaneously, i.e. in situ, bring about the hydrolysis of the ester groups to give hydroxyl groups, giving rise to a cellulose hydrate membrane.

Cellulose ester membranes may be composed of cellulose monoacetate, cellulose diacetate, cellulose triacetate, cellulose propionate, cellulose butyrate and cellulose acetobutyrate or other suitable cellulose esters or cellulose nitrate, methylcellulose or ethylcellulose, and mixtures of these.

After the hydrolysis, the resulting cellulose hydrate matrix is crosslinked, preferably by reacting the hydroxyl groups with one or more at least bifunctional reagent. Thereafter, functional groups (affinity ligands) are introduced into the crosslinked matrix so as to enable the separation of substances by adsorption.

In a further step, functional groups may be bound for example to the hydroxyl groups of the crosslinked membrane. Suitable methods for binding functional groups are known to the skilled worker.

By preference, functional groups are bonded to the cellulose membrane via epoxide groups or aldehyde groups. The epoxide groups may be introduced during the crosslinking step, or else thereafter.

It is especially preferred to use "Sartobind®" membranes from Sartorius Stedim Biotech GmbH in the method according to the invention.

Step (b), in which the plant extract is brought into contact with the microporous membrane, comprises all forms of bringing the plant extract into contact with the microporous membrane. Here, the bringing-into-contact is carried out in such a way that the phenolic secondary plant constituents are also brought into contact with the affinity ligands of the membrane so that they are adsorbed on to the latter. Step (b) can be carried out by passing the plant extract along at least one membrane surface, for example tangentially. However, when using a membrane with pores which extend from one main surface to the other main surface of the membrane, it is also possible to pass the plant extract across the membrane, which is preferably permeable to convection.

Within the scope of the present invention, the expression "adsorption" is understood as meaning all possibilities of the reversible binding of phenolic secondary plant constituents to the ligands. This reversible binding may be of the chemical and/or the physical type.

According to the present invention, step (c) includes the elution of the phenolic secondary constituents from the membrane. In this manner, a solution is obtained which comprises the phenolic secondary plant constituents. Within the scope of the present invention, the expression "elution" covers the desorption and the associated wash steps. The liquid used for elution is the "eluent".

Any solvent which has a higher affinity to the affinity ligands used than the phenolic secondary plant constituent to be isolated may be used in the method according to the invention as the eluent. In a preferred embodiment of the method according to the invention, the eluent is selected from the group consisting of aqueous sugar solutions and citric acid solutions. Sugar solutions which can be used are, for example, solutions of glucose, galactose and sorbitol. The advantage of using such toxicologically acceptable solvents is that the resulting solution can be used directly, i.e. without further treatment or processing, as a ready-to-use food additive. Thus, in a further preferred embodiment of the method according to the invention, the solvent is selected such that the solution obtained in step (c) which comprises the phenolic secondary plant constituents can be used directly, i.e. without further treatment or processing, as a ready-to-use food additive. Solutions which are suitable for this purpose, are, in particular, 1 M D-sorbitol solutions or 0.5 M citric acid monohydrate solutions.

If such a sugar solution is used as the eluant and, for example, phenyl boronate as the affinity ligand, then the phenyl boronate ligand which is fixed on the membrane interacts with cis-diols such as, for example, glucose, galactose or sorbitol which are present in the elution solution. The phenolic secondary plant constituents bound to the affinity ligands are thereby displaced from the ligand by an excess of, for example, sorbitol. This gives rise to a, for example, sorbitol-comprising solution of the phenolic secondary plant constituents as the eluate. This solution can be used directly as a ready-to-use food additive.

If, for example, a citric acid solution is used as the eluent and an iron (II) iminodiacetic acid complex as the affinity ligand, then not only are the phenolic secondary plant constituents eluted, but also in some cases the metal ions are liberated from the chelating agent fixed on the membrane, for example iminodiacetic acid, and these metal ions will pass into the eluate in the form of iron(II) citrate complexes with the phenolic secondary plant constituents. This gives rise to a ready-to-use food additive which is composed of the phenolic secondary plant constituents and a mineral additive (iron(II) citrate).

In a further preferred embodiment, the method according to the invention furthermore comprises, after step (b) and before step (c), the step of:
(b2) removing, from the plant extract, the plant residues remaining on the membrane by washing with an aqueous medium.

In this manner, the subsequent elution step can be simplified. Preferred aqueous media for this wash step are those which do not result in elution of the phenolic secondary plant constituents. Water in particular is preferred as the aqueous medium.

A further subject matter of the present invention relates to a food additive which can be obtained by the method according to the invention. Such a food additive comprises, for example, anthocyanins from plant material and D-sorbitol from the elution step, or iron(II) citrate complexes from the elution step.

A further subject matter of the present invention relates to the use of an inventive microporous membrane with affinity ligands for isolating phenolic secondary plant constituents from plant material.

The present invention is illustrated in greater detail with reference to the following nonlimiting examples.

Example 1

Preparation of a Plant Extract

The following text describes the preparation of an anthocyanin-comprising plant extract.

The plant extract was prepared from commercially available plums (*Prunus domestica*) (Unipack Fruits, South Africa). The fruits had a diameter of 7 to 8 cm, a fresh weight of approx. 150 to 200 g and were distinguished by a very dark purple fruit skin. Using three de-stoned fruits, the skin was removed from the fruit's body, and homogenized for 5 min in an "Ultra-Turrax® T25" disperser (Janke and Kunkel, Staufen im Breisgau) in 200 ml 10 mM HCl at an idling speed of 8000 rpm. This gave rise to a turbid suspension, giving rise to particles with an order of magnitude of no more than 0.5 mm. The particle size was determined with a transmitted-light microscope "Axiovert 40" (Zeiss) with a connected camera and the image analysis software "Axiovision" (Zeiss). This was not done to determine a size distribution, but only to ensure that the particles did not exceed the size of 0.5 mm. This suspension, hereinbelow termed "crude extract", was employed in the examples which follow.

Example 2

Preparation of a Microporous Membrane with Aminophenyl Boronate Ligands

The following text describes the preparation of a microporous membrane with aminophenyl boronate as the affinity ligand.

The membrane used was a polyester-nonwoven-reinforced cellulose acetate membrane (CA membrane) with a pore diameter of approx. 3 µm and which permits a water flow rate of 730 ml/(min×bar×cm2). The thickness of the membrane was 250 µm on average.

This CA membrane was hydrolyzed for 30 min at room temperature, using 0.6 M aqueous sodium hydroxide solution, and subsequently washed for 3×10 min using 0.5 M aqueous sodium hydroxide solution. The resulting membrane was treated (crosslinked) for 30 min at room temperature using aqueous 15% strength 1,4-butanediol diglycidyl ether in 0.5 M aqueous sodium hydroxide solution and 0.1% strength aqueous sodium borohydride solution. Thereafter, the moist membrane was left to stand in a sealed vessel for 20 h at room temperature. Finally, it was washed for 30 min in running water. Thereafter, the membrane was activated by a 30-minute treatment with a 1% strength aqueous sodium periodate solution at room temperature and then washed for 15 min in running water.

25 mg/ml sodium aminophenylboronate (FLUKA, Buchs, Switzerland; order No. 09199, batch 374599/50399) was dissolved in a buffer solution comprising 0.1 M citric acid and which had been brought to pH 5.6 with disodium hydrogen phosphate. 60 cm2 of the above-described membrane and 30 mg of NaCNBH3 (FLUKA, Buchs, Switzerland; order No. 71435, batch 1358598/21208152) were added to 3 ml of this solution and shaken for 60 min on an orbital shaker "Certomat® S" (Sartorius Stedim Biotech GmbH) at 60 rpm at ambient temperature. Thereafter, 50 mg of NaBH4 (FLUKA, Buchs, Switzerland; order No. 71321, batch 1171186/32105122) were added and shaking was continued for a further 15 min. Then, the membrane was washed three times for in each case 10 min, using 300 ml of water in each case. As the result, a cellulose hydrate membrane with aminophenyl boronate as the affinity ligand was obtained.

Example 3

Isolation of Anthocyanins 7 ml of crude extract of example 1 were added to the membrane obtained in example 2 and the mixture was shaken for 20 min on the above orbital shaker at 60 rpm at ambient temperature. During this process, the membrane turned purple-red. The membrane was then washed with 2×300 ml 10 mM HCl in water and then, together with 50 ml of a solution of 1 M D-sorbitol (ROTH, Karlsruhe, Art. No. 6213.1, batch 3499149) in 1 M HCl, shaken on the orbital shaker for 20 min at 60 rpm at ambient temperature. This gave a pink supernatant. The membrane was then washed with 3×300 ml of water and the experiment was repeated with the same membrane, twice in total (experiment 1 to experiment 3 in table 1). All the solutions and supernatants used were measured in a spectrophotometer at a wavelength of 520 nm, thereby determining the anthocyanin concentration. The results are compiled in table 1 hereinbelow. To this end, the absorption data of the respective fraction were converted into mg/l. In this context, a solution of 16 mg/l anthocyanin mixture at pH 2.5 generated an absorption of 0.45 at the wavelength 520 nm (L. Jurd, Food Sci. 29, 1964, pp. 16-19).

TABLE 1

Loading of an aminophenyl-boronate-reacted microporous membrane with an anthocyanin-comprising plant extract-results

|  | Experiment 1 | Experiment 2 | Experiment 3 |
|---|---|---|---|
| Starting solution+ [μg/total]+ | 785 | 2151 | 2151 |
| Final solution* [μg/total]+ | 129 | 938 | 1386 |
| Eluate [μg/total]+ | 624 | 804 | 219 |
| Recovery rate** [%] | 95 | 66 | 29 |

+corresponds to 7 ml of crude extract
*anthocyanin concentration in the supernatant above the membrane after 20 min shaking of the crude-extract-treated membrane
**= [c(eluate)/(c(starting solution) − c(final solution))] * 100%

During the course of the 3 experiments, the membrane color changed to bright red since colored constituents were irreversibly adsorbed. At the same time, the recovery rate and the binding capacity for the anthocyanins decreased in the course of experiments 1 to 3.

Example 4

Preparation of a Microporous Membrane with $Fe^{2+}$-Loaded Iminodiacetic Acid as the Ligand The following text describes the preparation of a microporous membrane with $Fe^{2+}$-loaded iminodiacetic acid as the affinity ligand.

A membrane circle with a diameter of 57 mm and with metal-chelate-forming groups of the iminodiacetic acid (IDA) type (reference No. 19442, batch 990136-3 R30A, Sartorius Stedim Biotech GmbH) was placed into 20 ml of a solution of 0.5 mol/l iron(II) chloride in water (E. Merck Darmstadt, order No. 1.03861.0250, batch F1114661 246) and shaken for 10 min on an orbital shaker "Certomat® S" (Sartorius Stedim Biotech GmbH) at 60 rpm at ambient temperature. As a result of the iron ion uptake, the membrane turned slightly pale yellow in color. Thereafter, the membrane was washed three times using 100 ml of water in each case. This gave a membrane with $Fe^{2+}$-complexed iminodiacetic acid as the affinity ligand. Example 5

Isolation of Anthocyanin

The membrane of example 4 was treated with 7 ml of crude extract of example 1 and shaken on the above orbital shaker for 10 min at 60 rpm and room temperature. During the course of this process, the membrane turned deep blue in color. Thereafter, the membrane was washed three times with in each case 100 ml of water. The membrane was treated with 29.5 ml of a solution of 0.5 mol/l citric acid monohydrate (Merck, Darmstadt) in 1 mol/l HCl and shaken on the orbital shaker for 15 min at 60 rpm and ambient temperature. In the course of this process, the membrane lost its color while the supernatant simultaneously turned pink.

The pink coloration of the supernatant was the result of the release of the anthocyanins which were fixed to the membrane by chelate formation with the iron(II)/iminodiacetic acid complex.

The experiment was repeated, using an identical membrane as per example 4. The results of the two experiments are compiled in table 2 hereinbelow. To this end, the absorption data of the respective fraction were converted into mg/l. In this context, a solution of 16 mg/l anthocyanin mixture at pH 2.5 generates an absorption of 0.45 at the wavelength 520 nm.

TABLE 2

Loading of a microporous membrane reacted with iminodiacetic acid and comprising iron(II) ions with an anthocyanin-comprising plant extract-results

|  | Experiment 1 | Experiment 2 |
|---|---|---|
| Starting solution [μg/total] | 1020 | 1450 |
| Final solution [μg/total] | 570 | 636 |
| Elution [μg/total] | 293 | 572 |
| Recovery rate [%] | 65 | 70 |

The definitions correspond to those given for table 1.

Example 6

Preparation of a Membrane Adsorber Module which Allows Particles to Pass and which Displays Chelate-Forming Ligands A membrane adsorber module which allows particles to pass was prepared analogously to German patent application DE 102 36 664 A1. To this end, a rectangular piece of the membrane described in example 4 (reference 19442, batch 990136-3 R30A, Sartorius Stedim Biotech GmbH) with a width of 8 cm and a length of 100 cm, together with a fabric of the type XNP 4410 (Convet Plastics bv, Genk, Belgium) of the same size, was wound on to a plastic rod of 1 cm in diameter, and this package was introduced in the center of a plastic tube 12 cm in length and 47 mm in diameter in such a way that the outermost membrane winding was in direct and liquid-impermeable contact with the inner tube wall. The result was a canal formed by the tissue and allowing particles to pass, which was bordered on both sides by the wound membrane. Circles 47 mm in diameter were punched out of the same tissue. In each case 8 of these circles were placed on the package on the approach-flow side and the discharge-flow side of the winding. The tube ends were sealed with rubber bungs of a suitable size provided with a central bore and with flexible tube fittings. The tube was placed vertically into a holder and a peristaltic pump was connected to the inlet tube fitting via a silicone tube. A suitable silicone tube was also connected to the discharge tube fitting. Both tubes were placed into a receiver vessel. The dead volume of the entire system composed of adsorber module and the tubes was 200 ml.

The receiver vessel was filled with 500 ml of water, and the latter was circulated for 5 min through the adsorber module at a flow rate of 300 ml/min. The water was discarded, 300 ml of fresh water was charged, and a solution of 1.5 g of iron(II) chloride (E. Merck, Darmstadt, order No. 1.03861.0250, batch F1114661 246) in water was added. The solution was circulated across the adsorber module as described above. Thereafter, the module was washed three times using 500 ml of water in each case, and the wash solution was discarded.

Example 7

Isolation of Anthocyanins

The skin of two commercially available plums (*Prunus domestica*) (Unipack Fruits, South Africa) were homogenized for 15 min in 150 ml of 10 mM HCl in an Ultra-Turrax® apparatus (Janke and Kunkel) at an idling speed of 8000 rpm. Thereafter, a further 850 ml of 10 mM HCl were added, and everything was mixed thoroughly and transferred into the receiving vessel of example 6. A turbid, deep red suspension resulted. Without further pretreatment, the suspension was circulated for 20 min across the adsorber module of example 6. Thereafter, 1 liter of a solution of 10 mM HCl was conveyed, in a linear stream, across the module until the discharge was clear and uncolored. The discharge was discarded.

Thereafter, 0.3 l of a solution of 1 M citric acid monohydrate in 1 M HCl (eluent) was placed into the receiving vessel, and this solution was circulated for 20 min across the adsorber module. Thereafter, the resulting elution solution was removed from the module with the exception of the residual volume retained in the membrane, and collected. A deep pink solution resulted. The module was washed with 2 l of water. The experiment was repeated, but only 10% of the crude extract (100 ml), based on the first experiment, were used.

The results are shown in table 3 below. The absorption data of the respective fraction were in each case converted into mg/l. In this context, a solution of 16 mg/l anthocyanin mixture at pH 2.5 generated an absorption of 0.45 at the wavelength 520 nm.

TABLE 3

Loading of an adsorber module which allows particles to pass and which comprises a microporous membrane reacted with iminodiacetic acid and comprising iron(II) ions, with an anthocyanin-comprising plum extract-results

|  | Experiment 1 | Experiment 2 |
| --- | --- | --- |
| Starting solution [µg/total] | 177 | 14.1 |
| Final solution [µg/total] | 143.8 | 9.4 |
| Wash solution [µg/total] | 9.6 | 1.7 |
| Eluate [µg/total] | 11 | 1.3 |
| Recovery rate** [%] | 47 | 43 |

**= [c(eluate)/(c(starting solution) − c(final solution)) − c(wash solution)] * 100%

The remaining definitions correspond to those given for table 1.

The results demonstrate that the membranes used here are suitable for isolating phenolic secondary plant constituents from plant material, obviating the need to clarify the suspension employed.

We claim:

1. A method of isolating phenolic secondary plant constituents from plant material, comprising the steps of:
    (a) providing homogenized plant parts as a plant extract which comprises phenolic secondary plant constituents,
    (b) bringing the plant extract into contact with a microporous membrane which has affinity ligands for the phenolic secondary plant constituents, whereby the phenolic secondary plant constituents are adsorbed on the membrane, and
    (c) eluting the phenolic secondary plant constituents from the membrane,
    whereby a solution comprising the phenolic secondary plant constituents is obtained wherein the affinity ligand of the membrane is selected from the group consisting of boronates and metal chelates.

2. The method as claimed in claim 1, wherein the plant material is selected from the group consisting of fruits, berries, vegetables, legumes, tubers, bulbs, beet/taproots, tea, cacao, coffee, timber, flowers, seeds, leaves and cones of conifers.

3. The method as claimed in claim 1, wherein the phenolic secondary plant constituents are selected from the group consisting of phenols;
    benzoquinones; hydroxybenzoic acids; acetophenones; tyrosines; phenylacetic acids; hydroxycinnamic acids; coumarins; isocoumarins; chromones; naphthoquinones;
    xanthones; stilbenes; anthraquinones; flavonoids selected from, flavones, flavonols, flavanols, flavanones, flavanonols, anthocyan ins, proanthocyan ins, isoflavonoids and biflavonoids; lignans; neolignans; lignins; catechol melanins; betalains; and chalcones.

4. The method as claimed in claim 3, wherein the phenolic secondary plant constituents are selected from the group consisting of L-DOPA as a phenol;
    hydroxybenzoic acids selected from salicylic acid, 4-hydroxybenzoic acid, gentisic acid, protocatechuic acid, gallic acid, vanillic acid, ellagic acid and hexahydroxydiphenic acid, and of their esters;
    hydroxycinnamic acids selected from coumaric acid, ferulic acid, caffeic acid, sinapic acid and rosmaric acid, and their esters and amides;
    resveratrol as a stilbene;
    flavonols selected from kaempferol, quercetin, myricetin and their arabinosides, galactosides, glucosides, glycosides, rhamnosides and xylosides;

flavanols selected from catechin, epicatechin, gallocatechin, epigallocatechin, theaflavin and their gallates;
flavanones selected from isosakuranetin, naringenin, hesperitin, eriodictyol, and their glycosides;
anthocyanins selected from the glycosides of pelargonidin, cyanidin, paeonidin, delphinidin, petunidin and malvidin;
proanthocyanins selected from the glycosides of the procyanidins and prodelphinidins;
isoflavones selected from genistein, daidzein, glycetein, and their glycosides; and
lignans selected from matairesinol and secoisolariciresinol diglucosides.

5. The method as claimed in claim 1, wherein the affinity ligand of the membrane is aminophenyl boronate and/or an iron(II)/iminodiacetic acid complex.

6. The method as claimed in claim 1, wherein the solvent used for the elution in step (c) is selected from the group consisting of aqueous sugar solutions and citric acid solutions.

7. The method as claimed in claim 1, wherein the solvent used for the elution in step (c) is chosen in such a way that the solution obtained in step (c), which comprises the phenolic secondary plant constituents, can be used directly as a ready-to-use food additive.

8. The method as claimed in claim 1, furthermore comprising, after step (a) and before step (b), the step of:
(a2) homogenizing the plant extract in such a way that the particles present in the plant extract have a size of no more than 0.5 mm.

9. The method as claimed in claim 1, furthermore comprising, after step (b) and before step (c), the step of:
(b2) removing, from the plant extract, plant residues remaining on the membrane by washing with an aqueous medium.

10. A method of isolating phenolic secondary plant constituents from plant material, comprising the steps of:
homogenizing plant material to provide a suspension of homogenized plant parts as a plant extract which comprises phenolic secondary plant constituents; then without clarifying the suspension
bringing the suspension of homogenized plant parts into contact with a microporous membrane which has affinity ligands for the phenolic secondary plant constituents, whereby the phenolic secondary plant constituents are adsorbed on the membrane; and then
eluting the phenolic secondary plant constituents from the membrane as a solution comprising the phenolic secondary plant constituents wherein the affinity ligand of the membrane is selected from the group consisting of boronates and metal chelates.

11. The method of claim 10 further comprising, after contacting the microporous membrane with the suspension and before eluting the phenolic secondary plant constituents, rinsing the microporous membrane with water.

12. The method of claim 10, wherein the microporous membrane is contacted with the homogenized plant parts without prefiltration.

13. The method of claim 10, wherein the microporous membrane is provided as a membrane absorber module that includes the microporous membrane bordering a canal through which particles can pass.

14. The method of claim 13, wherein the homogenized plant material is contacted with the microporous membrane by circulating through the canal of the membrane absorber module.

* * * * *